United States Patent
Kuroda et al.

(10) Patent No.: US 7,067,711 B2
(45) Date of Patent: Jun. 27, 2006

(54) ELONGATED ABSORBENT ARTICLE

(75) Inventors: Kenichiro Kuroda, Kagawa (JP); Jun Kudo, Kagawa (JP); Masataka Kinoshita, Kagawa (JP); Takuya Miyama, Kagawa (JP); Tatsuya Tamura, Kagawa (JP); Shimpei Komatsu, Kagawa (JP)

(73) Assignee: Uni-Charm Corporation, Shikokuchuo (JP)

( * ) Notice: Subject to any disclaimer, the term of this patent is extended or adjusted under 35 U.S.C. 154(b) by 0 days.

(21) Appl. No.: 11/058,460

(22) Filed: Feb. 14, 2005

(65) Prior Publication Data
US 2005/0148971 A1 Jul. 7, 2005

Related U.S. Application Data

(63) Continuation of application No. PCT/JP03/15388, filed on Dec. 2, 2003.

(30) Foreign Application Priority Data

Dec. 5, 2002 (JP) ............................. 2002-354181

(51) Int. Cl.
*A61F 13/20* (2006.01)
(52) U.S. Cl. .................. 604/380; 604/378; 604/379
(58) Field of Classification Search ............... 604/366, 604/378, 379, 380, 383, 385.201
See application file for complete search history.

(56) References Cited

U.S. PATENT DOCUMENTS

| | | | |
|---|---|---|---|
| 3,491,759 A * | 1/1970 | Samuel | 604/289 |
| 3,559,648 A * | 2/1971 | Mason, Jr. | 604/375 |
| 3,766,922 A * | 10/1973 | Krusko | 604/374 |
| 5,197,959 A * | 3/1993 | Buell | 604/385.23 |
| 5,439,458 A * | 8/1995 | Noel et al. | 604/378 |
| 5,591,150 A * | 1/1997 | Olsen et al. | 604/385.23 |
| 5,665,083 A * | 9/1997 | Igaue et al. | 604/370 |
| 5,702,378 A * | 12/1997 | Widlund et al. | 604/373 |
| 5,792,129 A * | 8/1998 | Johansson et al. | 604/387 |
| 5,830,296 A * | 11/1998 | Emenaker et al. | 156/219 |
| 5,873,868 A * | 2/1999 | Nakahata | 604/383 |
| 5,925,026 A * | 7/1999 | Arteman et al. | 604/383 |
| 5,977,430 A * | 11/1999 | Roe et al. | 604/378 |
| 5,998,696 A * | 12/1999 | Schone | 604/378 |
| 6,231,555 B1 * | 5/2001 | Lynard et al. | 604/385.01 |

(Continued)

FOREIGN PATENT DOCUMENTS

JP 05-228176 9/1993

(Continued)

*Primary Examiner*—Tatyana Zalukaeva
*Assistant Examiner*—Paula L. Craig
(74) *Attorney, Agent, or Firm*—Darby & Darby

(57) ABSTRACT

Disclosed is an elongated absorbent article, in which liquid passage holes and embossments are dispersed in a central region including a front portion and a rear portion. Aperture density obtained by dividing (total of areas occupied by the liquid passage holes in the front portion) by (area of the front portion) is higher than aperture density obtained by dividing (total of areas occupied by the liquid passage holes in the rear portion) by (area of the rear portion), while embossment density obtained by dividing (total of areas occupied by the embossments in the rear portion) by (area of the rear portion) is higher than embossment density obtained by dividing (total of areas occupied by the embossments in the front portion) by (area of the front portion).

11 Claims, 6 Drawing Sheets

U.S. PATENT DOCUMENTS

| | | | |
|---|---|---|---|
| 6,413,248 B1 * | 7/2002 | Mizutani | 604/385.17 |
| 6,423,884 B1 * | 7/2002 | Oehmen | 604/369 |
| 2002/0068894 A1 * | 6/2002 | Wada et al. | 604/15 |
| 2003/0088222 A1 * | 5/2003 | Yoshimasa et al. | 604/380 |
| 2003/0124311 A1 * | 7/2003 | Cree et al. | 428/138 |
| 2003/0167044 A1 * | 9/2003 | Toyoshima et al. | 604/367 |
| 2004/0030316 A1 * | 2/2004 | Gubernick et al. | 604/383 |

FOREIGN PATENT DOCUMENTS

| | | |
|---|---|---|
| JP | 06-126871 | 5/1994 |
| JP | 2001-095842 | 4/2001 |
| JP | 2001-129018 | 5/2001 |
| JP | 2002-360628 | 12/2002 |
| JP | 2003-275239 | 9/2003 |

* cited by examiner

ELONGATED ABSORBENT ARTICLE

CROSS REFERENCE TO RELATED APPLICATIONS

This application is a continuation of International Patent Application Serial No. PCT/JP03/15388, filed Dec. 12, 2003, which claims priority from Japanese Patent Application No. 2002-354181, filed Dec. 5, 2002.

BACKGROUND OF THE INVENTION

1. Field of the Invention

The present invention relates to an absorbent article suitable for absorbing menstrual blood and so on discharged from a woman's genital organ, more particularly, relates to an elongated absorbent article intended to cover the wearer's body from a vaginal opening to buttocks.

2. Description of the Related Art

Absorbent articles intended to absorb menstrual blood discharged from a woman's genital organ are typically constructed to include a liquid-permeable topsheet appearing on its skin surface, a liquid-impermeable backsheet appearing on its garment surface and a liquid absorbent layer disposed between the topsheet and the backsheet, and generally, they are worn with the backsheet adhered to an inner side of a groin piece of an undergarment through a pressure-sensitive adhesive layer.

In such an absorbent article, the function of certainly collecting menstrual blood applied to the skin surface is required so as to prevent lateral leakage of liquid and rearward leakage of liquid from the absorbent article.

Particularly in an absorbent article that is intended to be worn by a woman during menstruation while sleeping, required is not only prevention of lateral leakage of menstrual blood from the absorbent article but also prevention of leakage of menstrual blood trying to flow along the wearer's body toward the anus and the cleft of the buttocks or trying to flow along the skin surface of the absorbent article rearwardly. Accordingly, such an absorbent article for night-time use is elongated more than absorbent articles for daytime use so that its skin surface can cover a large area from a mons pubis which is anterior to the vaginal opening to the buttocks which is posterior to the anus, as disclosed in Japanese Unexamined Patent Publication Nos. 2001-95842 and 2001-129018.

In such an elongated absorbent article, frequently employed is a topsheet with liquid passage holes uniformly distributed over a large area from a portion intended to face the vaginal opening to a portion intended to face the anus and the cleft of the buttocks. For example, the topsheet is a nonwoven fabric in which liquid passage holes are uniformly distributed over a large area or a resin film in which liquid passage holes are uniformly distributed.

In the nonwoven fabric, however, the surface frictional strength will be deteriorated due to a large number of liquid passage holes formed therein, so that when a large force is applied to the rear portion fitting in the cleft of the buttocks due to a change in posture such as rolling over, fibers may be fluffed around the liquid passage holes and breakage may possibly occur around the liquid passage holes.

In the case of using the resin film with the liquid passage holes formed therein, on the other hand, if the resin film is thin and soft, the topsheet will be easily wrinkled due to the change in posture at its portion which is in dose contact with the anus and the cleft of the buttocks. In the case where such a thin resin film is used, therefore, the resin film and an underlying layer are bonded together through a hot-melt adhesive so as to constrain the resin film with the underlying layer. However, the hot-melt adhesive may result in obstruction to permeation of menstrual blood from the topsheet to the underlying layer.

In the elongated absorbent article designed to cover a large area from the vaginal opening to the cleft of the buttocks, therefore, the front portion intended to face the vaginal opening and receive a large amount of menstrual blood at a time need be able to rapidly introduce the menstrual blood into the liquid absorbent layer, while the rear portion intended to face the anus and the cleft of the buttocks need not be rapid in liquid absorption but need be effective in retaining a small amount of menstrual blood so as to prevent leakage. In addition, the rear portion need be of sufficient durability or bonding strength to prevent fluffing and occurrence of breakage or inhibit occurrence of wrinkles due to compression in the cleft of the buttocks and friction against the buttocks. As understood from above, it is not the best to uniformly distribute the liquid passage holes over the topsheet covering different portions that differ from one another in required function.

SUMMARY OF THE INVENTION

The present invention has been worked out in view of the shortcomings in the prior art set forth above. It is therefore an object of the present invention to provide an absorbent article in which rapid permeation of menstrual blood can be realized in a front portion intended to face the vaginal opening, while the function of inhibiting menstrual blood leakage and surface strength and bonding strength can be increased in a rear portion intended to face the cleft of the buttocks.

According to a first aspect of the present invention, there is provided an elongated absorbent article having a skin surface and a garment surface, comprising a liquid-permeable topsheet appearing on the skin surface, a backsheet appearing on the garment surface, and a liquid absorbent layer disposed between the topsheet and the backsheet, wherein compressed grooves where the liquid absorbent layer is compressed together with the topsheet are disposed to extend symmetrically about a longitudinal centerline of the absorbent article, defining therebetween an elongated central region, the central region including a front portion and a rear portion, wherein in the central region, a nonwoven fabric forming the topsheet is formed with liquid passage holes passing through at least the topsheet and dot-embossments where at least the topsheet is compressed, wherein aperture density obtained by dividing (total of areas occupied by the liquid passage holes in the front portion) by (area of the front portion) is higher than aperture density obtained by dividing (total of areas occupied by the liquid passage holes in the rear portion) by (area of the rear portion), while embossment density obtained by dividing (total of areas occupied by the embossments in the rear portion) by (area of the rear portion) is higher than embossment density obtained by dividing (total of areas occupied by the embossments in the front portion) by (area of the front portion).

In the absorbent article according to the first aspect of the present invention, since the topsheet is formed of a non-woven fabric, it can provide soft contact with the wearer's body. In a portion of the nonwoven fabric where the liquid passage holes are distributed, since menstrual blood can easily pass through the liquid passage holes under gravitation, permeation of menstrual blood can be made rapid. At the embossments formed in the nonwoven fabric, on the other hand, since the fiber density is significantly increased, menstrual blood can be strongly drawn in due to capillary action. That is, the liquid passage holes cannot provide a strong force to draw in menstrual blood but can provide rapid permeation of menstrual blood, while the embossments cannot provide rapid permeation of menstrual blood but can provide a strong force to draw in menstrual blood.

With a large number of liquid passage holes arranged in the front portion of the central region, menstrual blood discharged from the vaginal opening can be introduced into the liquid absorbent layer in a short period of time, and in the rear portion, menstrual blood coming from the front portion little by little can be retained by the embossments to prevent leakage.

With a large number of embossments arranged in the rear portion, furthermore, the surface frictional strength of the nonwoven fabric can be increased in the rear portion, so that when a force from the cleft of the buttocks is applied to the rear portion, fluffing and occurrence of breakage can be prevented. In addition, since the embossments are not many in the number in the front portion, the possibility that the embossments will come into contact with the vaginal opening and so on can be reduced, so that the front portion becomes less irritating to the vaginal opening and so on but comfortable to wear.

The absorbent article according to the first aspect of the present invention may be constructed such that topsheet comprises heat-fusible fibers and a second layer comprising heat-fusible fibers is disposed beneath the topsheet, wherein the liquid passage extend from the topsheet into the second layer and the topsheet and the second layer are fusion-bonded together along inner surfaces of the liquid passage holes, while the topsheet and the second layer are compressed and fusion-bonded together at the embossments.

In this case, since the topsheet and the second layer are bonded together around the liquid passage holes, the topsheet is reinforced with the second layer, so that even when applied a force from the wearer's body, the topsheet hardly causes wrinkles, preventing occurrence of breakage in the topsheet from the liquid passage holes. Accordingly, the individual liquid passage holes may have a large opening size. With the embossments where the topsheet and the second layer are compressed together being formed in the rear portion, the topsheet is also reinforced with the second layer in the rear portion. Moreover, when the topsheet and the second layer are compressed together, surrounding portions of the embossments become so bulky that the embossments hardly give a stiff feel to the wearer's body.

In order to exhibit the reinforcing function and to be bulky, as set forth above, it is preferred that the second layer has a larger basis weight than the topsheet.

The absorbent article according to the first aspect of the present invention may also be constructed such that the liquid passage holes are present but the embossments are absent in the front portion.

With only the liquid passage holes being present in the front portion, the whole front portion can be made soft, providing soft, improved contact with the vaginal opening and its surroundings.

In this case, it is preferred that average center-to-center distance between adjacent embossments in the rear portion is larger than average center-to-center distance between adjacent liquid passage holes in the front portion.

If the aperture density of the liquid passage holes is increased in the front portion, menstrual blood discharged from the vaginal opening can be rapidly introduced into the liquid absorbent layer through the liquid passage holes. On the other hand, since the amount of menstrual blood trying to migrate to the rear portion is less than the amount of menstrual blood given to the front portion, rearward migration can be sufficiently prevented even if the embossment density is low. With the embossment density being lowered in the rear portion, furthermore, the rear portion can be prevented from being excessively stiffened, providing soft contact with the wearer's body.

According to a second aspect of the present invention, there is provided an elongated absorbent article having a skin surface and a garment surface, comprising a liquid-permeable topsheet appearing on the skin surface, a backsheet appearing on the garment surface, and a liquid absorbent layer disposed between the topsheet and the backsheet, wherein compressed grooves where the liquid absorbent layer is compressed together with the topsheet are disposed to extend symmetrically about a longitudinal centerline of the absorbent article, defining therebetween an elongated central region, the central region including a front portion and a rear portion, wherein liquid passage holes are uniformly distributed in the topsheet over the central region while dot-embossments where the topsheet is compressed are arranged in the central region in such a manner that embossment density obtained by dividing (total of areas occupied by the embossments in the rear portion) by (area of the rear portion) is higher than embossment density obtained by dividing (total of areas occupied by the embossments in the front portion) by (area of the front portion).

Also in this absorbent article according to the second aspect of the present invention, since the embossments are arranged mainly in the rear portion, the embossments hardly irritate the vaginal opening and its surroundings. Moreover, menstrual blood trying to migrate rearwardly can be drawn in by the embossments of a high density.

In the second aspect of the present invention, the topsheet should not be limited to one formed of a nonwoven fabric, but may be a resin film formed with the liquid passage holes.

In this case, the embossments can improve the bond between the topsheet and an underlying layer so as to prevent the occurrence of wrinkles in the topsheet due to friction against the cleft of the buttocks and so on. Furthermore, since the density of the layer underlying the topsheet can be increased by the embossments, menstrual blood trying to migrate rearwardly can be retained by such high-density portions.

Preferably, a second layer comprising heat-fusible fibers is disposed beneath the topsheet being the resin film, wherein the topsheet and the second layer are compressed and fusion-bonded together at the embossments.

In this construction, the topsheet being the resin film and the second layer can be integrated without using an excessive amount of hot-melt adhesive in the rear portion, and the fiber density of the second layer can be increased at the embossments so that menstrual blood can be strongly drawn in at the embossments.

If the absorbent article is constructed such that the embossments are absent in the front portion, moreover, the front portion in close contact with the vaginal opening and its surroundings hardly irritate the wearer's skin.

As has been described hereinabove, the present invention is suitable for an elongated absorbent article, in which the front portion is intended to face a vaginal opening of a wearer, while the rear portion is intended to face a portion posterior to the vaginal opening.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "longitudinal centerline" refers to a line which extends longitudinally to divide the absorbent article laterally in two. On the other hand, the term "lateral reference line" does not necessarily refer to a line which extends laterally to divide the absorbent article longitudinally in two, but refers to a line which extends laterally to cross a longitudinal center of a portion intended to be brought into contact with the vaginal opening during wear.

As shown in the following embodiments, the absorbent article has a central region formed with liquid passage holes and embossments, wherein the number of liquid passage holes per unit area (the unit area can be determined arbitrarily, e.g., 100 mm$^2$) and the number of embossments per unit area are referred to as "number density of the liquid passage holes" and "number density of the embossments", respectively.

Furthermore, the central region can be divided into front and rear portions, wherein (total of areas occupied by the liquid passage holes in the front portion)/(area of the front portion) is referred to as "aperture density in the front portion", (total of areas occupied by the liquid passage holes in the rear portion)/(area of the rear portion) is referred to as "aperture density in the rear portion", (total of areas occupied by the embossments in the front portion)/(area of the front portion) is referred to as "embossment density in the front portion", and (total of areas occupied by the embossments in the rear portion)/(area of the rear portion) is referred to as "embossment density in the rear portion".

Figure 1:
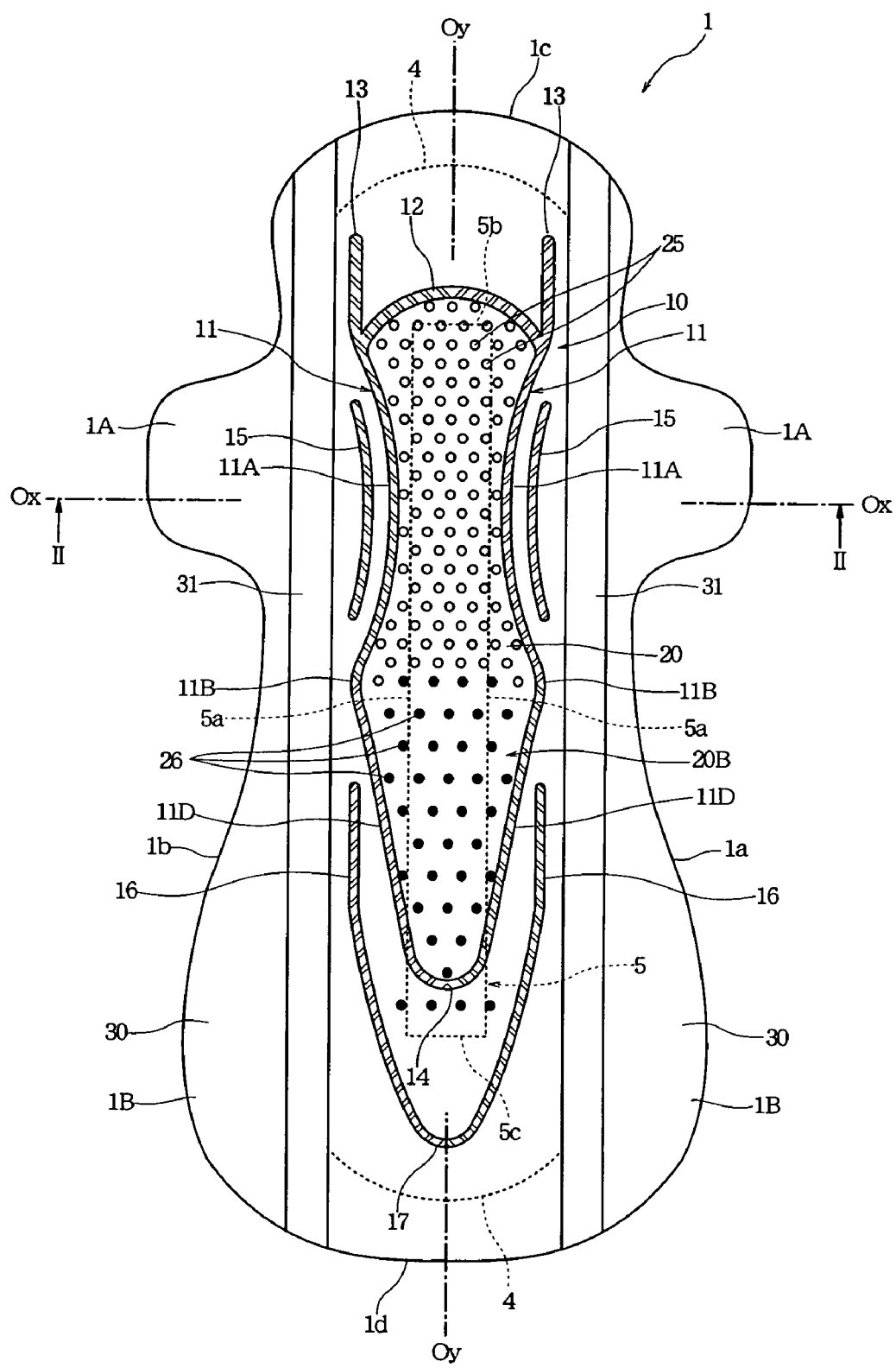
FIG. 1 is a top plan view showing a sanitary napkin as an absorbent article according to a first embodiment of the present invention.
Figure 2:
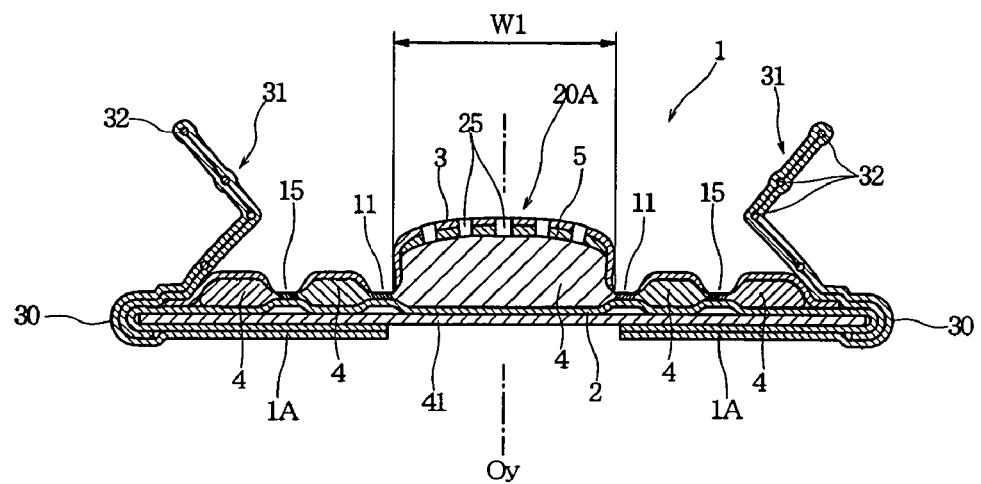
FIG. 2 is a sectional view taken along line II—II (lateral reference line), showing a state where the sanitary napkin of FIG. 1 is attached to a crotch portion of an undergarment.
Figure 3:
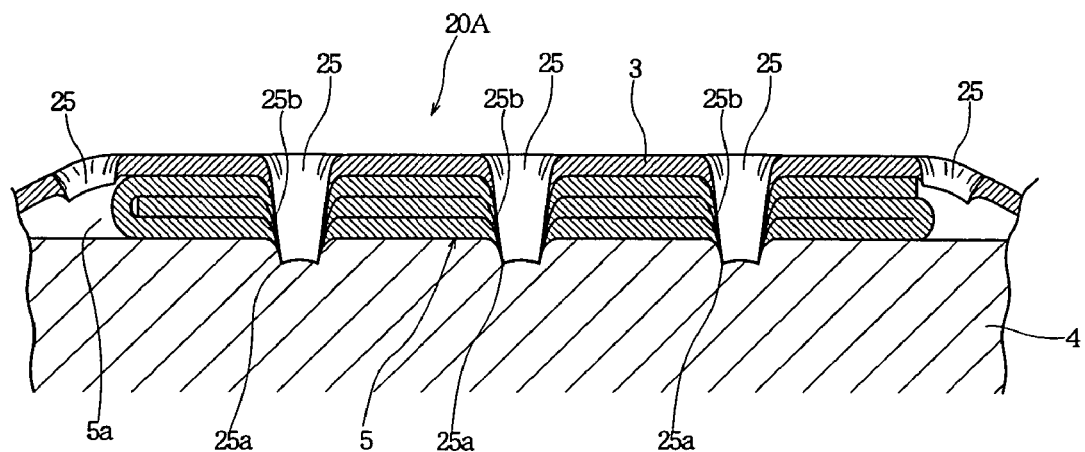
FIG. 3 is an enlarged sectional view showing how liquid passage holes are apertured in a front portion.
Figure 4:
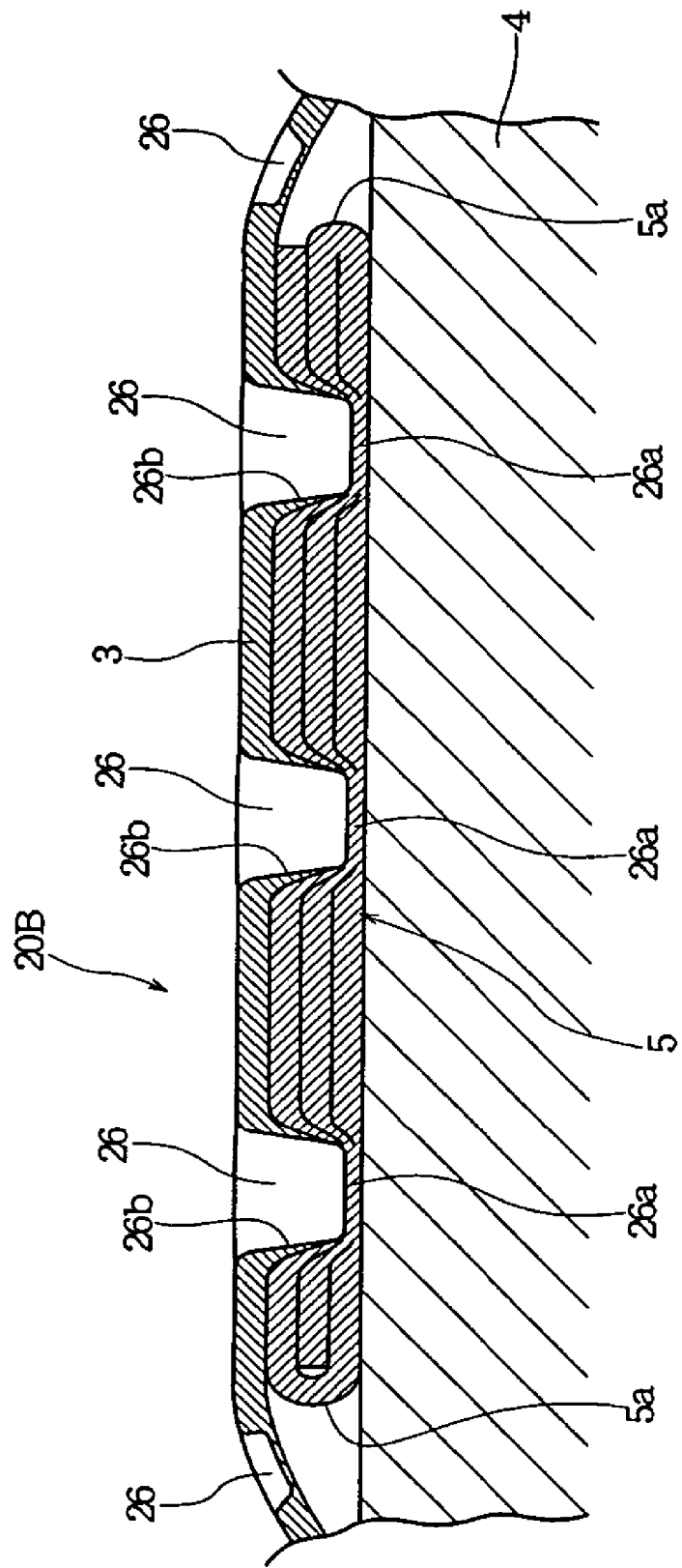
FIG. 4 is an enlarged sectional view showing how embossments are formed in a rear portion.

FIG. 1 is a top plan view showing a sanitary napkin 1 as an absorbent article according to a first embodiment of the present invention, wherein the skin surface faces upward; FIG. 2 is a sectional view taken along line II—II (lateral reference line), showing a state where the sanitary napkin of FIG. 1 is attached to a groin piece of an undergarment; FIG. 3 is an enlarged sectional view of the sanitary napkin showing a front portion of a central region; and FIG. 4 is an enlarged sectional view of the sanitary napkin showing a rear portion of the central region.

The sanitary napkin 1 of FIG. 1 is an elongated sanitary napkin that is suitable for nighttime use by a woman during menstruation, wherein the entire length in the longitudinal direction is from about 200 to 380 mm.

The sanitary napkin 1 has longitudinally extending right and left side edges 1a and 1b that are laterally spaced an equal distance apart from a longitudinal centerline Oy-Oy and outwardly curved front and rear end edges 1c and 1d that are longitudinally spaced apart from a lateral reference line Ox-Ox. The distance from the lateral reference line Ox-Ox to the rear end edge 1d is larger than the distance from the lateral reference line Ox-Ox to the front end edge 1c.

Within a range having a given length in the longitudinal direction and containing the lateral reference line Ox-Ox, the right and left side edges 1a and 1b project laterally outwardly, thereby providing wings 1A and 1A. Rearward of the wings 1A and 1A, furthermore, the right and left side edges 1a and 1b are curved to gradually rearwardly increase the lateral separation distance therebetween, thereby providing rear flaps 1B and 1B.

As shown in the sectional view of FIG. 2, the sanitary napkin 1 comprises a liquid-impermeable backsheet 2 appearing on the garment surface and a liquid-permeable topsheet 3 appearing on the skin surface. A liquid absorbent layer 4 is disposed between the backsheet 2 and the topsheet 3, and a second layer 5 is disposed between the topsheet 3 and the liquid absorbent layer 4. As indicated by a dotted line in FIG. 1, the liquid absorbent layer 4 extends over a large area from a position just inside the front end edge 1c to a position just inside the rear end edge 1d, but for the wings 1A, 1A and the rear flaps 1B, 1B.

In the sanitary napkin 1, compressed groove 10 is formed in the skin surface by locally pressing and heating at least the topsheet 3 and the liquid absorbent layer 4. More specifically, the compressed groove 10 is formed by embossing with a heating roller. After the liquid absorbent layer 4 is stacked on the topsheet 3, a smooth surface roller is applied to a surface of the liquid absorbent layer 4 while a heating roller with projections arranged in a pattern for embossing is applied to a surface of the topsheet 3 for pressing and heating.

The compressed groove 10 has high-density compressed portions, in which the liquid absorbent layer 4 and the topsheet 3 are pressed until they get almost filmy, and medium-density compressed portions, in which although doesn't get filmy, the liquid absorbent layer 4 is of a higher density than in portions other than the compressed groove 10. The high-density compressed portions and the medium-density compressed portions alternate with each other to provide continuously recessed grooves where the skin surface of the sanitary napkin 1 is recessed toward the side of the backsheet 2.

As shown in FIG. 1, the compressed groove 10 has several distinct compressed grooves indicated by numerals 11–17.

Longitudinally extending inner compressed grooves 11 and 11 are disposed symmetrically about the longitudinal centerline Oy-Oy. The inner compressed grooves 11 and 11 include front curved portions 11A and 11A, inflected portions 11B and 11B and rear oblique portions 11D and 11D. The front curved portions 11A and 11A are curved toward the longitudinal centerline Oy-Oy so that separation distance therebetween is minimum at the lateral reference line Ox-Ox. As the front curved portions 11A and 11A extend rearwardly (toward the rear end edge 1d) from the lateral reference line Ox-Ox, the separation distance between the inner compressed grooves 11 and 11 gradually increases. Then, the separation distance becomes largest at the inflected portions 11B and 11B and gradually decreases rearwardly from the inflected portions 11B and 11B to provide the rear oblique portions 11D and 11D.

At front ends of the front curved portions 11A and 11A, the right and left inner compressed grooves 11 and 11 are connected to each other through a front connecting compressed groove 12. The front connecting compressed groove 12 is curved toward the front end edge 1c.

From boundaries between the front curved portions 11A and 11A and the front connecting compressed groove 12, extension compressed grooves 13 and 13 are further extended toward the front end edge 1c. The extension compressed grooves 13 and 13 are disposed symmetrically about the longitudinal centerline Oy-Oy.

At rear ends of the rear oblique portions 11D and 11D, the inner compressed grooves 11 and 11 are connected to each other through a rear connecting compressed groove 14. The rear connecting compressed groove 14 is curved toward the rear end edge 1d.

Thus, the inner compressed grooves 11 and 11, the front connecting compressed groove 12, the extension compressed grooves 13 and 13 and the rear connecting compressed groove 14 are mutually connected. In addition, a given area of the skin surface of the sanitary napkin 1 is surrounded by the inner compressed grooves 11 and 11, the front connecting compressed groove 12 and the rear connecting compressed groove 14, and this surrounded area is referred to as central region 20. The central region 20 is of an elongated shape symmetrical about the longitudinal centerline Oy-Oy, wherein a portion forward of the lateral reference line Ox-Ox is shorter than a portion rearward of the lateral reference line Ox-Ox.

Front outer compressed grooves 15 and 15 are disposed at positions spaced laterally apart from the front curved portions 11A and 11A of the inner compressed grooves 11 and 11. The front outer compressed grooves 15 and 15 are within a range having a given length forwardly and rearwardly from the lateral reference line Ox-Ox. The front outer compressed grooves 15 and 15 are curved similarly to the front curved portions 11A and 11A.

At positions spaced laterally apart from the rear oblique portions 11D and 11D of the inner compressed grooves 11 and 11, on the other hand, there are disposed rear outer compressed grooves 16 and 16. The rear outer compressed grooves 16 and 16 are inclined to gradually decrease separation distance therebetween toward the rear end edge 1d, and the right and left rear outer compressed grooves 16 and 16 are connected to each other through a rear connecting compressed groove 17. The rear outer compressed grooves 16 and 16 and the rear connecting compressed groove 17 are continuously formed, wherein the rear connecting compressed groove 17 is curved toward the rear end edge 1d.

Figure 6:
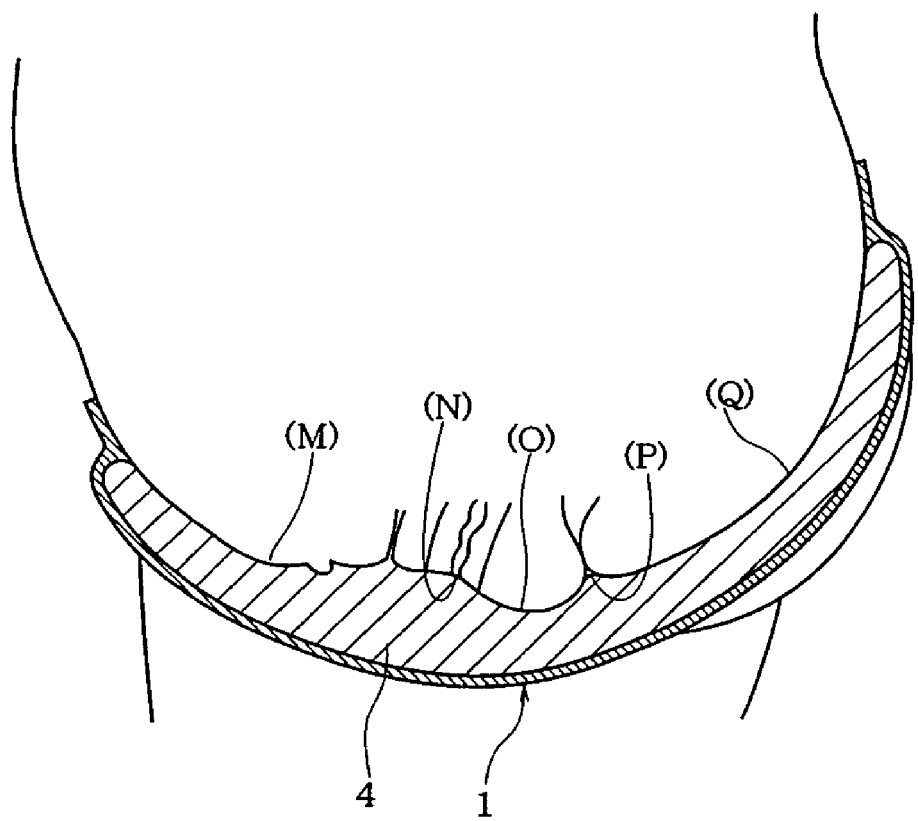
FIG. 6 is an explanatory sectional view showing a state where the sanitary napkin is applied to the wearer's body.

The central region 20 includes a front portion 20A and a rear portion 20B. The position of the boundary between the front portion 20A and the rear portion 20B and the lengths of the front portion 20A and the rear portion 20B may vary according to the length of the sanitary napkin 1. When applied to the woman's body as shown in FIG. 6, the front portion 20A faces the vaginal opening (N), while the rear portion 20B faces a portion including the anus (P) and the cleft (Q) of the buttocks without facing the vaginal opening (N).

In the embodiment shown in FIG. 1, the front portion 20A extends from a line connecting between the peaks of the inflected portions 11B and 11B of the inner compressed grooves 11 and 11 to the front connecting compressed groove 12, while the rear portion 20B extends from the line connecting between the peaks of the inflected portions 11B and 11B to the rear connecting compressed groove 14.

As shown in FIG. 1, the second layer 5 is disposed within the central region 20 and is of a rectangular shape with its long sides extending along the longitudinal direction of the article, wherein right and left side edges 5a and 5a being the long sides of the second layer 5 are spaced apart from the inner compressed grooves 11 and 11 toward the longitudinal centerline Oy-Oy so that the second layer 5 does not overlap with the inner compressed grooves 11 and 11. A front end edge 5b being one short side of the second layer 5 is positioned slightly closer to the lateral reference line Ox-Ox than the front connecting compressed groove 12 so that the second layer 5 does not overlap with the front connecting compressed groove 12. On the other hand, a rear portion of the second layer 5 traverses the rear connecting compressed groove 14 so that a rear end edge 5c being the other short side of the second layer 5 is positioned rearward of the rear connecting compressed groove 14 but forward of the rear connecting compressed groove 17.

It should be noted that the front portion of the second layer 5 may traverse the front connecting compressed groove 12 so that the front end edge 5b is positioned between the front connecting compressed groove 12 and the front end edge 1c and that the front end edge 5b of the second layer 5 may reach the front end edge 1c of the sanitary napkin 1 and the rear end edge 5c reach the rear end edge 1d of the sanitary napkin 1.

In the central region 20: a large number of liquid passage holes 25 are regularly arranged in the front portion 20A; a large number of dot-embossments 26 are regularly arranged in the rear portion 20B. In FIG. 1, the embossments 26 are indicated by black circles for the convenience of distinguishing between the liquid passage holes 25 and the embossments 26 in the drawings. However, the embossments 26 should not be construed as being blacked out in an actual product.

In the front portion 20A, the liquid passage holes 25 are present but the embossments 26 are absent. In the front portion 20A, therefore, no embossments 26 are disposed between adjacent liquid passage holes 25. However, the liquid passage holes 25 and the embossments 26 may be mixed within a limited area along the boundary between the front portion 20A and the rear portion 20B, as shown in FIG. 1.

In the present embodiment, the individual liquid passage holes 25 are of circular shape, but the liquid passage holes 25 may be of elliptical shape. Alternatively, the individual liquid passage holes 25 may be formed in the shape of a short slit.

In the present embodiment, provided in the rear portion 20B are only the embossments 26. That is, the liquid passage holes 25 are not provided in the rear portion 20B. However, the liquid passage holes 25 may be mixed with the embossments 26 in the rear portion 20B. In the case where the liquid passage holes 25 are formed in the rear portion 20B, it is preferred that the number of the liquid passage holes 25 is smaller than the number of the embossments 26 in the rear portion 20B. Alternatively, it is preferred that the aperture density obtained by dividing (total of areas occupied by the liquid passage holes 25 in the rear portion 20B) by (area of the rear portion 20B) is lower than the embossment density obtained by dividing (total of areas occupied by the embossments 26 in the rear portion 20B) by (area of the rear portion 20B).

In the present embodiment, the individual shape of the dot-embossments (i.e., embossments arranged in a dot pattern) 26 is circular. However, the dot-embossments as used herein should not be construed as limited to circular embossments, but may be otherwise shaped, such as elliptical or short line-shaped.

When the front portion 20A and the rear portion 20B are compared per unit area, on the other hand, the number of the embossments 26 per unit area in the rear portion 20B is smaller than the number of the liquid passage holes 25 per unit area in the front portion 20A. That is, the number density of the embossments 26 in the rear portion 20B is lower than the number density of the liquid passage holes 25 in the front portion 20A.

On the other hand, the embossment density in the rear portion 20B obtained by dividing (total of areas occupied by the embossments 26 in the rear portion 20B) by (area of the rear portion 20B) is lower than the aperture density in the front portion 20A obtained by dividing (total of areas occupied by the liquid passage holes 25 in the front portion 20A) by (area of the front portion 20A). In the embodiment shown in FIG. 1, furthermore, the average center-to-center distance between adjacent embossments 26 in the rear portion 20B is larger than the average center-to-center distance between adjacent liquid passage holes 25 in the front portion 20A. It should be noted that the area of the individual embossments 26 is larger than the area of the individual liquid passage holes 25.

Each liquid passage hole 25 has an opening area of 0.2 to 8 mm$^2$, and in case of circle, it has a diameter of 0.5 to 3.2 mm. The center-to-center distance between adjacent liquid passage holes 25 is 2 to 8 mm. At its bottom 26a, each embossment 26 has an area of 2 to 10 mm$^2$, and in case of circle, it has a diameter of 1.6 to 3.6 mm. The center-to-center distance between adjacent embossments 26 is 3 to 10 mm.

In order that menstrual blood given to the front portion 20A will be rapidly and evenly introduced into the liquid absorbent layer 4, it is preferred that the number density of the liquid passage holes 25 does not vary with the location in the front portion 20A and that the liquid passage holes 25 are regularly uniformly distributed, as shown in FIG. 1. The aperture density in the front portion 20A is 6 to 20%. On the other hand, the region over which the liquid passage holes 25 are distributed should have a width of at least 10 mm in a lateral direction perpendicular to the longitudinal centerline Oy-Oy. If it is less than the above-mentioned range, it will be difficult to introduce a sufficient amount of menstrual blood discharged from the vaginal opening into the liquid absorbent layer 4.

In the rear portion 20B, on the other hand, the number density of the embossments 26 may vary with the location. For example, the number density of the embossments 26 may be high at a position near the rear connecting compressed groove 14 but low at a position near the inflected portions 11B and 11B.

FIG. 3 shows how the liquid passage holes 25 are apertured in the front portion 20A and FIG. 4 shows how the embossments 26 are formed in the rear portion 20B.

In the front portion 20A, the liquid passage holes 25 are formed to pass through the topsheet 3 and reach the second layer 5, and preferably, the liquid passage holes 25 are formed to pass through both the topsheet 3 and the second layer 5, as shown in FIG. 3. In regions outside the side edges 5a and 5a of the second layer 5, on the other hand, the liquid passage holes 25 are formed only in the topsheet 3.

In the rear portion 20B, as shown in FIG. 4, the topsheet 3 and the second layer 5 are compressed and recessed toward the liquid absorbent layer 4 to form the embossments 26. In regions outside the side edges 5a and 5a of the second layer 5, on the other hand, the embossments 26 are formed with only the topsheet 3 being compressed and recessed toward inside of the napkin.

The topsheet 3 comprises heat-fusible, thermoplastic fibers, and the second layer 5 also comprises heat-fusible, thermoplastic fibers. Here, the topsheet 3 and the second layer 5 should not be construed as limited to a sheet/layer formed only of such thermoplastic fibers, but may contain other fibers that are not heat-fusible, such as natural fibers and regenerated cellulose fibers, in addition to the thermoplastic fibers.

The liquid passage holes 25 can be formed using heated needles or pins. More specifically, the liquid passage holes 25 can be formed in such a way that after the topsheet 3 and the second layer 5 are stacked, the needles or pins are inserted in a direction from the topsheet 3 to the second layer 5 and then drawn out to leave terminal ends 25a projecting downwardly. At this time, the thermoplastic fibers contained in the topsheet 3 and the thermoplastic fibers contained in the second layer 5 are fusion-bonded together along inner surfaces 25b of the liquid passage holes 25 and therearound. This results in that the opening shape of the liquid passage hole 25 becomes stable and that the portion around the opening of the liquid passage hole 25 is reinforced with the second layer 5. In addition, since the topsheet 3 and the second layer 5 are thermally fusion-bonded together, there is no need for bonding the topsheet 3 and the second layer 5 together through an adhesive, precluding the possibility that the adhesive will interfere with liquid permeation.

After formation of the liquid passage holes 25, the topsheet 3 and the second layer 5 are held between heated rolls to form the embossments 26. At this time, a smooth surface roller is applied to the surface of the second layer 5 while an embossing roller having projections is applied to the surface of the topsheet 3. Thus, the thermoplastic fibers contained in the topsheet 3 and the thermoplastic fibers contained in the second layer 5 are fusion-bonded together along inner surfaces 26b of the embossments 26, and additionally, the fiber density of the topsheet 3 and the fiber density of the second layer 5 are increased at portions around the inner surfaces 26b.

At the bottoms 26a of the embossments 26, the fibers constituting the topsheet 3 and the fibers constituting the second layer 5 are compressed to have a high density, wherein the thermoplastic fibers are melted so that the bottoms 26a can get filmy or almost filmy.

Due to the fusion-bonding of the thermoplastic fibers at the inner surfaces 26b and the bottoms 26a, the shape of the embossments 26 becomes stable and the topsheet 3 is reinforced with the second layer 5. Particularly since the density is increased at the bottoms 26a, the durability of the topsheet 3 is improved.

The topsheet 3 may be through-air bonded nonwoven fabric. For the through-air bonded nonwoven fabric, sheath/core bicomponent synthetic fibers, of which the core component is polyethylene terephthalate (PET) containing titanium oxide and the sheath component is polyethylene (PE), are bonded together by means of hot air to have a basis weight of about 15 to 60 g/m². It should be noted that some of the bicomponent synthetic fibers used for the topsheet 3 are coated with a hydrophilic lubricant while the rest are coated with a water-repellent lubricant and they are blended with each other, wherein the blending ratio of the fibers coated with the water-repellent lubricant is preferably 10 to 30% by weight. With the fibers coated with the water-repellent lubricant uniformly contained in the topsheet 3 to have a blending ratio within the above-mentioned range, menstrual blood given to the topsheet 3 can be prevented from being excessively diffused in the topsheet 3, so that in the front portion 20A, menstrual blood can be introduced into the liquid absorbent layer 4 mainly through the liquid passage holes 25.

It should be noted that the topsheet 3 is permeable to menstrual blood also in the region other than the liquid passage holes 25 for introduction into the second layer 5. In order to provide the topsheet 3 with such permeability to liquid, the density is preferably equal to or less than 0.12 g/cm³, wherein the lower limit is about 0.025 g/cm³.

The second layer 5 may be through-air bonded nonwoven fabric comprising eccentric sheath/core bicomponent synthetic fibers, of which the core component is polypropylene (PP) and the sheath component is polyethylene (PE). In the through-air bonded nonwoven fabric for the second layer 5, all the fibers are coated with a hydrophilic lubricant. That is, fibers coated with a water-repellent lubricant are not contained. In the embodiment shown in FIGS. 3 and 4, the second layer 5 is formed by stacking a plurality of layers of the through-air bonded nonwoven fabric, such as by folding a single through-air bonded nonwoven fabric in three-ply construction. The single through-air bonded nonwoven fabric has a basis weight of about 15 to 50 g/m², so that the second layer 5 has a basis weight of about 45 to 150 g/m².

With the basis weight of the second layer 5 made higher than the basis weight of the topsheet 3, the topsheet 3 can be reinforced with the second layer 5, thereby preventing occurrence of extremely large wrinkles in the topsheet 3 and occurrence of breakage from the liquid passage holes 25.

For example, the topsheet 3 may comprise fibers having a fineness of 2.2 dtex and the second layer 5 may comprise fibers having a fineness of 4.4 dtex so that the fiber density of the second layer 5 is lower than the fiber density of the topsheet 3. The fiber density of the second layer 5 is 0.016 to 0.08 g/cm³.

Alternatively, the topsheet 3 and the second layer 5 may be nonwoven fabric other than the through-air bonded nonwoven fabric. For example, the topsheet 3 may be spunlaced nonwoven fabric comprising regenerated cellulose fibers, heat-fusible thermoplastic fibers and optionally also pulp; the second layer 5 may be air-laid nonwoven fabric, in which pulp and thermoplastic fibers are accumulated in air, bonded together with a binder, and pressed between heating rollers.

The liquid absorbent layer 4 may be formed by adding synthetic absorbent polymer such as polyacrylate, polyacrylamide and maleic anhydride or natural absorbent polymer such as starch and cellulose to an aggregate of pulp such as ground pulp, mercerized pulp or crosslinked pulp, wherein the pulp and the synthetic absorbent polymer or the like are wrapped in hydrophilic tissue paper.

The backsheet 2 is a liquid-impermeable, breathable sheet such as a polyethylene (PE) or polypropylene (PP) film formed with minute pores. The minute pores may be appropriately distributed over the film for improving breathability such as by adding inorganic filler such as $CaCO_3$ and $BaSO_4$ to the plastic sheet, followed by drawing. The film may have a thickness of about 15 to 50 μm.

The second layer 5 and the liquid absorbent layer 4 are bonded together through a hot-melt adhesive that is partially applied so as not to interfere with liquid permeation. The liquid absorbent layer 4 and the backsheet 2 are also bonded together through a hot-melt adhesive.

In a manufacturing process of the sanitary napkin 1, after the topsheet 3 and the second layer 5 are stacked and the liquid passage holes 25 and the embossments 26 are formed in the order named above or vice versa, the liquid absorbent layer 4 and the second layer 5 are bonded together and then the compressed groove 10 is formed therein. Subsequently, the backsheet 2 is bonded to a surface of the liquid absorbent layer 4.

On the skin surface, as shown in FIG. 2, liquid-impermeable sheets 30 and 30 are provided at right and left sides thereof. In the wings 1A, 1A and the rear flaps 1B, 1B, the liquid-impermeable sheets 30 and 30 are bonded to the surface of the backsheet 2 through a hot-melt adhesive. At positions spaced laterally equally apart from the longitudinal centerline Oy-Oy, the liquid-impermeable sheets 30 are folded in two with longitudinally extending elastic members 32 bonded to the inside. Due to the elastic members 32, an elastic shrinkage force acts between front and rear portions of the sanitary napkin 1 to curve the sanitary napkin 1, which results in rising of the liquid-impermeable sheets 30 and 30 at an intermediate portion between the front and rear portions of the sanitary napkin, thereby forming leakage preventing walls 31 and 31.

The liquid-impermeable sheets may be spunbonded nonwoven fabric, meltblown nonwoven fabric, or composite nonwoven fabric being a laminate thereof.

The basis weight of the liquid absorbent layer 4 becomes largest at the central region 20. The basis weight at the portions located between the inner compressed grooves 11, 11 and the front outer compressed grooves 15, 15, the basis weight at the portions located between the inner compressed grooves 11, 11 and the rear outer compressed grooves 16, 16 and the basis weight at the portion located between the rear connecting compressed groove 14 and the rear connecting compressed groove 17 are all lower than the basis weight at the central region 20. The basis weight of the liquid absorbent layer 4 at the other portions is equal to or slightly lower than that at the portions located between the inner compressed grooves 11, 11 and the front outer compressed grooves 15, 15 and so on.

The basis weight of the liquid absorbent layer 4 at the central region 20 is preferably 400 to 1200 g/m$^2$, more preferably 500 to 1000 g/m$^2$. The basis weight at the portions located between the inner compressed grooves 11, 11 and the front outer compressed grooves 15, 15, the basis weight at the portions located between the inner compressed grooves 11, 11 and the rear outer compressed grooves 16, 16 and the basis weight at the portion located between the rear connecting compressed groove 14 and the rear connecting compressed groove 17 are preferably 300 to 900 g/m$^2$, more preferably 350 to 600 g/m$^2$. The basis weight of the liquid absorbent layer 4 at the other portions is preferably 300 to 700 g/m$^2$.

As a result, the thickness is increased in the central region 20 so that the skin surface bulges toward the wearer's body in the central region 20, as shown in FIG. 2.

The length of the central region 20, i.e., the longitudinal distance between the front connecting compressed groove 12 and the rear connecting compressed groove 14 is about 120 to 300 mm. The width of the central region 20 on the lateral reference line Ox-Ox, i.e., the minimum width W1 of the front portion 20A shown in FIG. 2 is decided according to the width of the woman's genital organ. Because the crotch width of average women is about 30 mm, the width W1 is preferably in the range of 15 to 50 mm, more preferably in the range of 20 to 40 mm. On the other hand, the lateral distance between the inflected portions 11B, 11B of the inner compressed grooves 11, 11 is larger than the width W1 by about 10 to 40 mm. The lateral distance between the side edges 5a, 5a of the second layer 5 is smaller than the width W1 by 1 to 10 mm.

The rear portion 20B of the central region 20 is so dimensioned as to easily enter the woman's cleft (Q) of the buttocks shown in FIG. 6, so that its length, i.e., the length from the inflected portions 11B, 11B to the rear connecting compressed groove 14 is about 60 to 150 mm.

When the sanitary napkin 1 is to be attached to the wearer's body, a pressure-sensitive adhesive provided on the exterior surface of the backsheet 2 is adhered to the inner side of the groin piece 41 shown in FIG. 2, and at this time, the rear flaps 1B, 1B are also adhered to the inner side of the undergarment. On the other hand, the wings 1A, 1A are folded back against an outer side of the undergarment to cover both side edges of the groin piece 41, and adhered to the outer side of the groin piece 41 through a pressure-sensitive adhesive provided on the garment surface of the wings 1A, 1A.

As shown in FIG. 6, when the undergarment is worn with the sanitary napkin 1 attached to the groin piece 41, the woman's crotch will be covered with the skin surface of the sanitary napkin 1 from the mons pubis (M) to the portion posterior to the cleft (Q) of the buttocks.

As shown in FIG. 2, the central region 20 located between the inner compressed grooves 11 and 11 bulges toward the wearer's body to be bulkier than the other regions. Therefore, the front portion 20A of the bulky central region 20 can easily come into close contact with the vaginal opening (N), wherein it is preferred that the portion traversed by the lateral reference line Ox-Ox comes into close contact with the center of the vaginal opening (N). On the other hand, the widened portion located between the inflected portions 11B and 11B of the inner compressed grooves 11 and 11 mainly comes into contact with the perineum (O), and the rear portion 20B of the central region 20 comes into contact with the anus (P) and the cleft (Q) of the buttocks.

The topsheet 3 appearing on the skin surface in the central region 20 is low-density through-air bonded nonwoven fabric and beneath it, there is provided the second layer 5 that is bulky through-air bonded nonwoven fabric. Therefore, the central region 20 can provide soft contact with the respective portions of the wearer's body. Particularly because the embossments 26 are not present in the front portion 20A, the embossments will never come into contact with and irritate the vaginal opening and its surroundings. In addition, since the embossments 26 in the rear portion 20B are deeply recessed into the second layer 5, the high-density portions at the bottoms 26a of the embossments 26 arranged in the rear portion 20B hardly come into direct contact with the wearer's body. Therefore, the possibility that the embossments 26 will irritate the perineum (O), the anus (P) and the cleft (Q) of the buttocks can also be lowered.

Menstrual blood discharged from the vaginal opening (N) is mainly given to the front portion 20A of the central region 20. Since the topsheet 3 is low-density nonwoven fabric, menstrual blood permeates through the topsheet 3, but diffusion of menstrual blood in the topsheet 3 is restrained due to the presence of the fibers coated with the water-repellent lubricant in the topsheet 3. Menstrual blood given to the topsheet 3 can migrate to the second layer 5 that underlies and is in close contact with the topsheet 3, wherein since the second layer 5 is through-air bonded nonwoven fabric having voids therein, menstrual blood passes through the voids in the second layer 5 under gravitation and is then drawn in by the underlying liquid absorbent layer 4. However, most of menstrual blood given to the front portion 20A can rapidly pass through the liquid passage holes 25 and is then drawn in by the liquid absorbent layer 4 that underlies and is in close contact with the second layer 5.

Thus, menstrual blood discharged from the vaginal opening (N) can be rapidly absorbed by the liquid absorbent layer 4 in the front portion 20A. In a lying posture, however, there will be menstrual blood trying to flow beyond the perineum (O) to the anus (P) and the cleft (Q) of the buttocks. When a large amount of menstrual blood is given to the front portion 20A at a time, furthermore, part of the menstrual blood sometimes migrates to the rear portion 20B along the surface of the topsheet 3.

Menstrual blood having migrated to the rear portion 20B will be strongly drawn in due to capillary action of the high-density portions around the embossments 26, wherein since the high-density portions extend from the topsheet 3 to the second layer 5, menstrual blood can move along the high-density portions from the topsheet 3 to the second layer 5, and is then drawn in and retained by the underlying liquid absorbent layer 4 of high hydrophilicity. Although the liquid passage holes 25 are not formed in the rear portion 20B, the amount of menstrual blood that can reach the rear portion 20B will be sufficiently smaller than the amount of menstrual blood given to the front portion 20A, so that menstrual blood flowing rearwardly can be sufficiently collected by the embossments 26 that are dotted over the rear portion 20B. Thus, rearward leakage of menstrual blood can be prevented.

Here, it should be noted that since the rear portion 20B comes into close contact with the area from the anus (P) to the cleft (Q) of the buttocks, a lateral compressive force will be repeatedly exerted on the rear portion 20B according to the movement of the buttocks. Moreover, a significant change in posture such as rolling over while sleeping will also exert a pressure on the rear portion 20B, and such a pressure is inconstant. Due to the presence of the embossments 26, however, the durability of the topsheet 3 is enhanced in the rear portion 20B and additionally, the topsheet 3 is reinforced with the second layer 5. Therefore, worries about occurrence of large wrinkles in the rear portion 20B, fluffing of the surface and occurrence of breakage can be eliminated.

Figure 5:
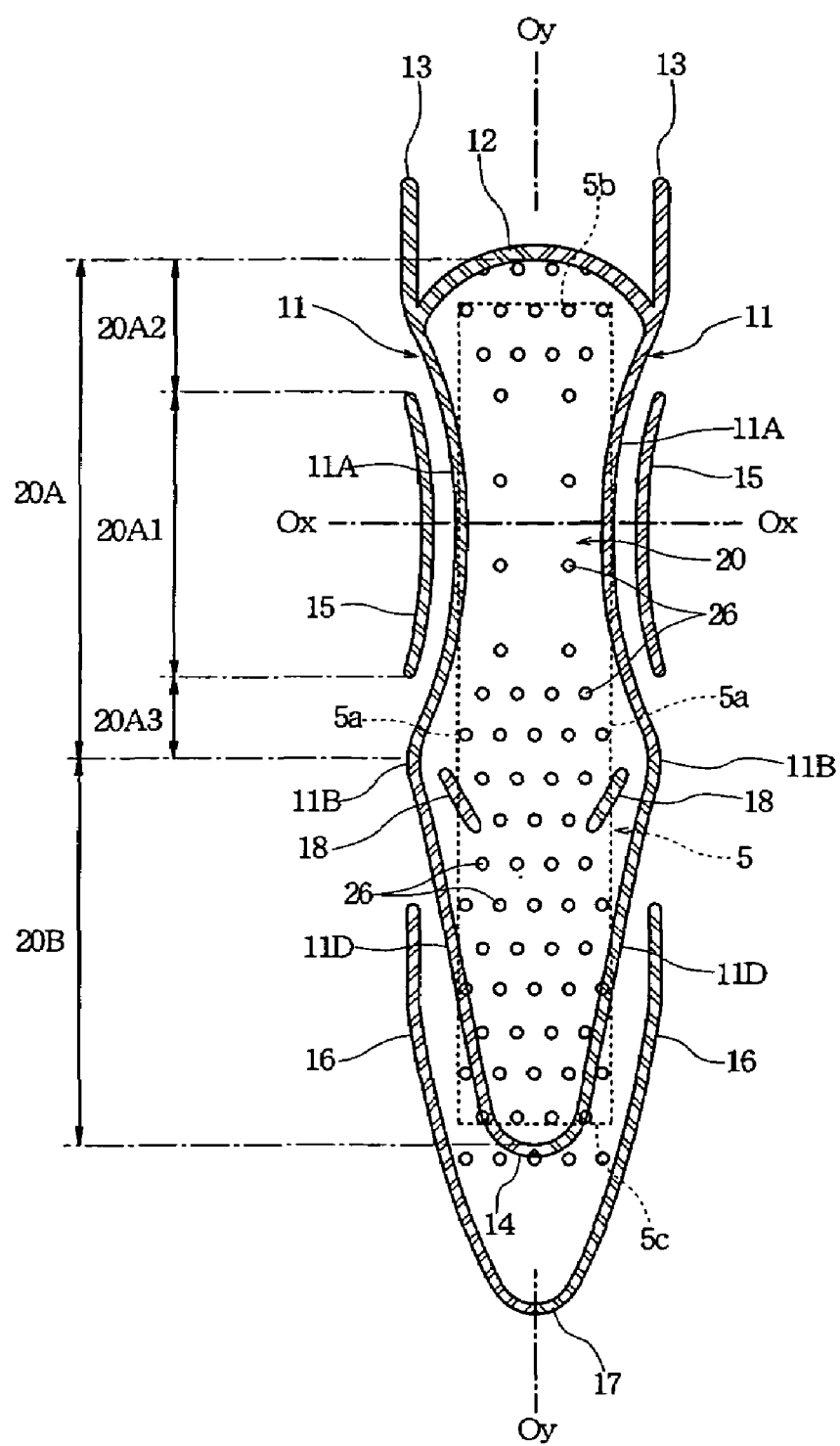
FIG. 5 is a top plan view showing a portion of sanitary napkins according to second and third embodiments of the present invention.

FIG. 5 is a top plan view showing a portion of a sanitary napkin according to other embodiments of the present invention.

In FIG. 5, only a portion containing the compressed grooves 11–17, the central region 20 and the second layer 5 is shown. The other portions having the same construction as those of the sanitary napkin 1 according to the first embodiment of FIG. 1 are not shown in the figure. It should be noted that the compressed grooves 11–17 shown in FIG. 5 are similar in shape and construction to those of the first embodiment shown in FIG. 1.

As shown in FIG. 5 (and as described in the first embodiment of FIG. 1), the central region 20 surrounded by the inner compressed grooves 11, 11, the front connecting compressed groove 12 and the rear connecting compressed groove 14 has the front portion 20A forward of the inflected portions 11B, 11B and the rear portion 20B rearward of the inflected portions 11B, 11B. In the present embodiment, furthermore, the front portion 20A has three regions: a first front portion 20A1; a second front portion 20A2 forward of the first front portion 20A1; and a third front portion 20A3 rearward of the first front portion 20A1, wherein the boundary between the first and second front portions 20A1 and 20A2 and the boundary between the first and third front portions 20A1 and 20A3 are equally spaced apart from the lateral reference line Ox-Ox in the longitudinal direction.

In this sanitary napkin, the first front portion 20A1 is intended to face the vaginal opening (N) and the third front portion 20A3 is intended to face a portion posterior to the vaginal opening (N). In this specification, since a portion of the central region 20 positioned rearward of its portion intended to face the vaginal opening can be defined as rear portion of the central region 20, the portion indicated by 20A3 may be included in the rear portion 20B. In the embodiment shown in FIG. 5, however, the portion indicated by 20A3 is distinguished from the rear portion 20B and called "third front portion" as set forth above.

In FIG. 5, the embossments 26 arranged in the central region 20 are indicated by white circles that are not blacked out. Here, the liquid passage holes are omitted from the drawing.

The individual embossments 26 are formed in the same area, but the number density, i.e., the number of embossments 26 per unit area is small in the first front portion 20A1 intended to contact the vaginal opening but large in the rear portion 20B, the second front portion 20A2 and the third front portion 20A3.

If (total of areas occupied by the embossments 26 in the first front portion 20A1)/(area of the first front portion 20A1) is referred to as embossment density A1, (total of areas occupied by the embossments 26 in the second front portion 20A2)/(area of the second front portion 20A2) is referred to as embossment density A2, (total of areas occupied by the embossments 26 in the third front portion 20A3)/(area of the third front portion 20A3) is referred to as embossment density A3, and (total of areas occupied by the embossments 26 in the rear portion 20B)/(area of the rear portion 20B) is referred to as embossment density B, on the other hand, the embossment density A1 is lower than any of the embossment densities A2, A3 and B. In this embodiment, furthermore, the embossment densities A2, A3 and B are almost equal. The embossment density A1 is preferably equal to or less than ⅕, more preferably equal to or less than 1/10 the embossment densities A2, A3 and B.

Accordingly, the embossment density obtained by dividing (total of areas occupied by the embossments 26 in the front portion 20A) by (area of the front portion 20A) is lower than the embossment density obtained by dividing (total of areas occupied by the embossments 26 in the rear portion 20B) by (area of the rear portion 20B), wherein the former is preferably equal to or less than ⅕, more preferably equal to or less than 1/10 the latter.

In the embodiment of FIG. 5, short compressed grooves 18 and 18 are formed at positions rearward of the inflected portions 11B and 11B of the inner compressed grooves 11 and 11 and spaced inwardly apart from the rear oblique portions 11D and 11D. Also in the short compressed grooves 18 and 18, the topsheet 3 and the liquid absorbent layer 4 are compressed to have high-density compressed portions and medium-density compressed portions alternating with each other, as in the individual compressed grooves 11–17.

In the rear portion 20B, therefore, the short compressed grooves 18, 18 are provided along with the dot-embossments 26, but in the definition of the embossment density of the dot-embossments 26, areas of the short compressed grooves are not included in total of areas occupied by the embossments 26.

As sanitary napkins with the embossments 26 arranged in the pattern of FIG. 5, the following second and third embodiments may be provided.

In the second embodiment, the topsheet 3 covering the central region 20 is formed of the same nonwoven fabric as in the first embodiment of FIG. 1, and the liquid passage holes 25 passing through both the topsheet 3 and the second layer 5 are formed therein, as shown in FIG. 3. The liquid passage holes 25 may be distributed over the front portion 20A as in FIG. 1 or may be uniformly distributed over the first and second front portions 20A1 and 20A2. In the second embodiment, furthermore, the liquid passage holes 25 may be provided also in the rear portion 20B.

However, the aperture density obtained by dividing (total of areas occupied by the liquid passage holes 25 in the front portion 20A) by (area of the front portion 20A) should be higher than the aperture density obtained by dividing (total of areas occupied by the liquid passage holes 25 in the rear portion 20B) by (area of the rear portion 20B). Also, the embossment density obtained by dividing (total of areas occupied by the embossments 26 in the rear portion 20B) by (area of the rear portion 20B) should be higher than the embossment density obtained by dividing (total of areas occupied by the embossments 26 in the front portion 20A) by (area of the front portion 20A). This is further illustrated in FIG. 7, which in addition illustrates liquid passage holes 26 which are uniformly distributed over the central region 20 of the topsheet 8.

Figure 7:
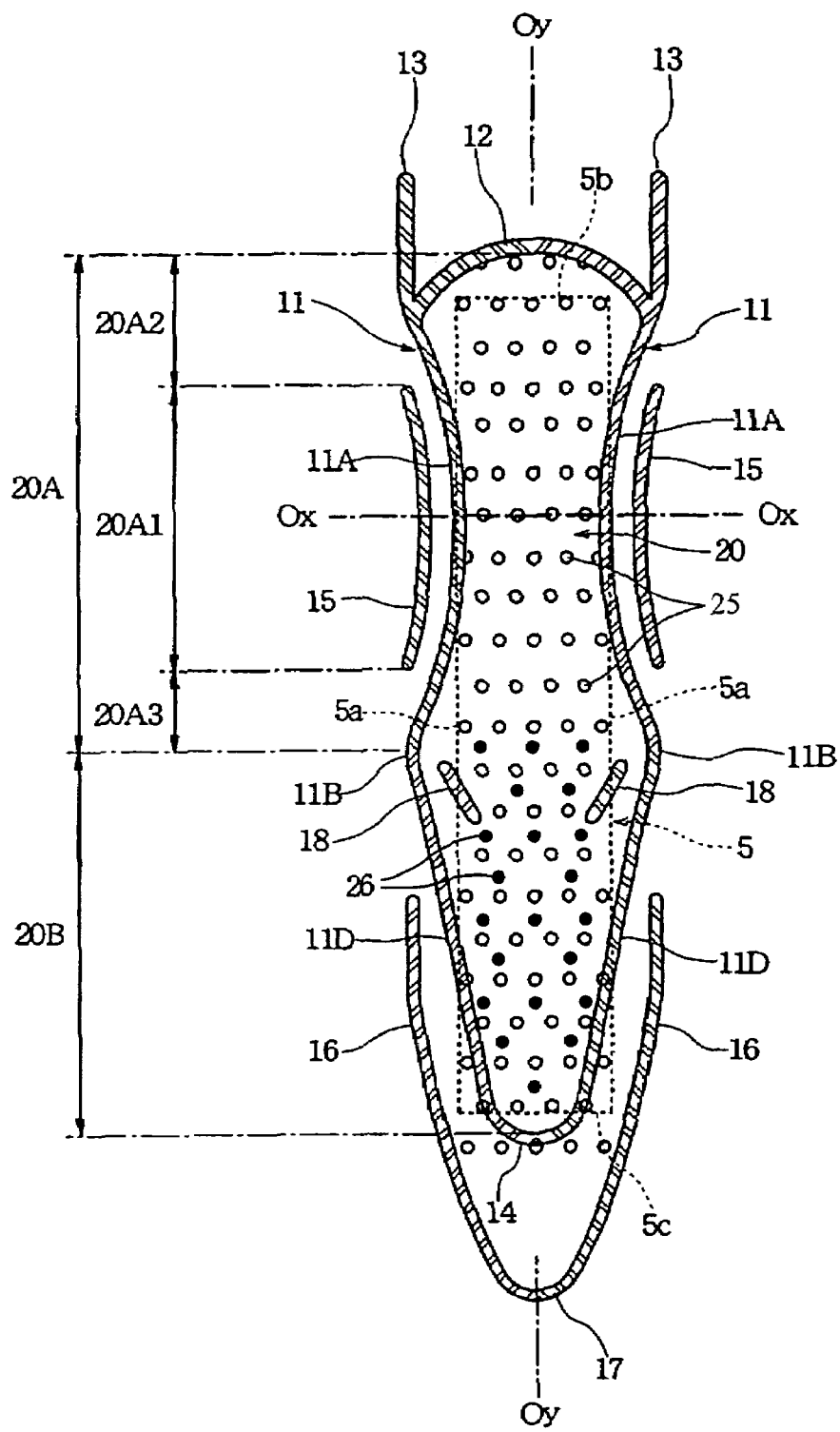
FIG. 7 is a top plan view showing a portion of a sanitary napkin according to another embodiment of the invention.

This is true for the case where the range indicated by 20A1 and 20A2 is defined as the front portion, while the range indicated by the 20A3 and 20B is defined as thr rear portion in each of FIGS. 5 and 7.

Since a large number of liquid passage holes 25 are thus present in the front portion 20A, menstrual blood can rapidly pass through the liquid passage holes 25 in the front portion 20A, particularly in the first front portion 20A1, under gravitation into the liquid absorbent layer 4. In addition, since the number of the embossments 26 is small in the front portion 20A, particularly in the first front portion 20A1, the possibility that the embossments 26 will come into contact with the vaginal opening can be lowered.

On the other hand, since a large number of embossments 26 are present in the rear portion 20B, fluffing of the topsheet 3 in the rear portion 20B and occurrence of breakage from the liquid passage holes 25 can be prevented even when the rear portion 20B fitting in the cleft of the buttocks is subjected to a pressure or frictional force from the wearer's body.

Furthermore, since the number density of the embossments 26 is increased in the second and third front portions 20A2 and 20A3 that are positioned forward and rearward of the first front portion 20A1 where the number of the embossments 26 is small and the liquid passage holes 25 are predominantly present as shown in FIG. 5, the topsheet is reinforced at positions forward and rearward of the first front portion 20A1, thereby preventing the topsheet from causing extremely large wrinkles or from breaking from the liquid passage holes 25 in the first front portion 20A1.

In the third embodiment of the present invention, the topsheet covering the central region 20 of FIG. 5 is formed of resin film having liquid passage holes.

For example, the resin film may be polyethylene film that is clouded due to titanium oxide contained therein and is of a thickness of about 15 to 50 μm. A large number of liquid passage holes may be formed therein in such a way that softened resin film is supplied to the surface of a drum having a large number of apertures, followed by air suction from inside of the drum. The individual liquid passage holes may be circular or elliptical. Alternatively, the resin film may be of a network structure so that meshes can serve as liquid passage holes. Preferably, the average opening size of the individual liquid passage holes is 0.2 to 2 mm and the aperture density of the liquid passage holes is 10 to 30%.

In the case where the resin film having a large number of liquid passage holes is used for the topsheet 3 to cover the central region 20 (and the other regions) in FIG. 5, the liquid passage holes can be uniformly distributed over the central region 20.

In this case, the resin film and the underlying second layer are heated together under pressure at the embossments 26 of FIG. 5, so that the topsheet 3 of the resin film is integrated with the second layer 5 at the embossments 26. In addition, the fiber density of the second layer 5 is increased at the embossments 26.

Also in the third embodiment, menstrual blood in the front portion 20A can rapidly pass through the liquid passage holes formed in the resin film and through spaces between fibers in the second layer 5 under gravitation into the liquid absorbent layer 4. In addition, since the number of the embossments 26 is small in the front portion 20A, particularly in the first front portion 20A1, the possibility that the embossments 26 will come into contact with the vaginal opening can be lowered.

Also in the rear portion 20B, menstrual blood can rapidly migrate to the liquid absorbent layer 4 through the liquid passage holes formed in the topsheet 3, but at the same time, the menstrual blood is strongly drawn in by a large number of embossments 26 where the fiber density of the second layer 5 is increased. In the rear portion 20B, furthermore, since the topsheet 3 and the second layer 5 are bonded together at a large number of embossments 26 provided therein, occurrence of extremely large wrinkles in the topsheet 3 formed of the resin film can be prevented even when the rear portion 20B fitting in the cleft of the buttocks is subjected to a pressure or frictional force from the wearer's body.

Here, the topsheet 3 of the resin film and the second layer 5 are bonded together through a hot-melt adhesive to improve the degree of adhesion, but since the topsheet 3 and the second layer 5 are bonded together at the embossments 26 as well, the application amount of the hot-melt adhesive can be decreased, thereby eliminating the possibility that the hot-melt adhesive will interfere with liquid permeation from the topsheet 3 to the second layer 5.

For example, the right and left inner compressed grooves 11 and 11 may be independent each other without providing the front connecting compressed groove 12 and the rear connecting compressed groove 14.

According to the present invention, as has been described hereinabove, menstrual blood can be certainly collected by the elongated central region between the compressed grooves, effectively preventing rearward migration of menstrual blood. In addition, the durability of the topsheet can be enhanced in the central region, eliminating worries about occurrence of extremely large wrinkles or breakage due to a force from the wearer's body.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An elongated absorbent article having a skin surface and a garment surface, comprising a liquid-permeable topsheet appearing on the skin surface, a backsheet appearing on the garment surface, and a liquid absorbent layer disposed between the topsheet and the backsheet, wherein compressed grooves where the liquid absorbent layer is compressed together with the topsheet are disposed to extend symmetrically about a longitudinal centerline of the absorbent article, defining therebetween an elongated central region, the central region including a front portion and a rear portion, wherein in the central region, a nonwoven fabric forming the topsheet is formed with liquid passage holes passing through at least the topsheet and dot-embossments where at least the topsheet is compressed, wherein aperture density obtained by dividing (total of areas occupied by the liquid passage holes in the front portion) by (area of the front portion) is higher than aperture density obtained by dividing (total of areas occupied by the liquid passage holes in the rear portion) by (area of the rear portion), while embossment density obtained by dividing (total of areas occupied by the embossments in the rear portion) by (area of the rear portion) is higher than embossment density obtained by dividing (total of areas occupied by the embossments in the front portion) by (area of the front portion).

2. An elongated absorbent article as set forth in claim 1, wherein the topsheet comprises heat-fusible fibers and a second layer comprising heat-fusible fibers is disposed beneath the topsheet, wherein the liquid passage holes extend from the topsheet into the second layer and the topsheet and the second layer are fusion-bonded together along inner surfaces of the liquid passage holes, while the topsheet and the second layer are compressed and fusion-bonded together at the embossments.

3. An elongated absorbent article as set forth in claim 2, wherein the second layer has a larger basis weight than the topsheet.

4. An elongated absorbent article as set forth in claim 1, wherein the liquid passage holes are present but the embossments are absent in the front portion.

5. An elongated absorbent article as set forth in claim 4, wherein average center-to-center distance between adjacent embossments in the rear portion is larger than average center-to-center distance between adjacent liquid passage holes in the front portion.

6. An elongated absorbent article having a skin surface and a garment surface, comprising a liquid-permeable topsheet appearing on the skin surface, a backsheet appearing on the garment surface, and a liquid absorbent layer disposed between the topsheet and the backsheet, wherein
compressed grooves where the liquid absorbent layer is compressed together with the topsheet are disposed to extend symmetrically about a longitudinal centerline of the absorbent article, defining therebetween an elongated central region, the central region including a front portion and a rear portion, wherein
liquid passage holes are uniformly distributed in the topsheet over the central region while dot-embossments where the topsheet is compressed are arranged in the central region in such a manner that embossment density obtained by dividing (total of areas occupied by the embossments in the rear portion) by (area of the rear portion) is higher than embossment density obtained by dividing (total of areas occupied by the embossments in the front portion) by (area of the front portion).

7. An elongated absorbent article as set forth in claim 6, wherein the topsheet is a resin film formed with the liquid passage holes.

8. An elongated absorbent article as set forth in claim 7, wherein a second layer comprising heat-fusible fibers is disposed beneath the topsheet, wherein the topsheet and the second layer are compressed and fusion-bonded together at the embossments.

9. An elongated absorbent article as set forth in claim 6, wherein the embossments are absent in the front portion.

10. An elongated absorbent article as set forth in claim 1, wherein the front portion is intended to face a vaginal opening of a wearer, while the rear portion is intended to face a portion posterior to the vaginal opening.

11. An elongated absorbent article as set forth in claim 6, wherein the front portion is intended to face a vaginal opening of a wearer, while the rear portion is intended to face a portion posterior to the vaginal opening.

* * * * *